(12) United States Patent
Roempke

(10) Patent No.: US 6,213,990 B1
(45) Date of Patent: Apr. 10, 2001

(54) URINE AND EXCRETA DISPOSAL DEVICE AND METHOD OF USE

(76) Inventor: Heinz Roempke, Kastanienallee 16, 23669 Timmendorfer Strand (DE)

( * ) Notice: Subject to any disclaimer, the term of this patent is extended or adjusted under 35 U.S.C. 154(b) by 0 days.

(21) Appl. No.: 09/063,896

(22) Filed: Apr. 22, 1998

(30) Foreign Application Priority Data

Apr. 23, 1997 (DE) ............................................. 197 17 853

(51) Int. Cl.[7] ....................................................... A61F 5/44
(52) U.S. Cl. ........................... 604/332; 604/337; 604/341
(58) Field of Search ................................... 604/332, 346, 604/347, 337, 338, 339, 341; 4/144.1, 144.3

(56) References Cited

U.S. PATENT DOCUMENTS

| 3,077,883 | * | 2/1963 | Hill ........................................ 604/347 |
|---|---|---|---|
| 4,608,046 | | 8/1986 | Towfigh . |
| 4,681,573 | * | 7/1987 | McGovern et al. ................. 604/329 |
| 5,065,459 | * | 11/1991 | Tjahaha et al. ........................ 4/144.2 |
| 5,346,482 | * | 9/1994 | Metz et al. ........................... 604/338 |
| 5,742,948 | * | 4/1998 | Cicio .................................... 4/144.3 |

FOREIGN PATENT DOCUMENTS

| 4343789C2 | 8/1997 | (DE) . |
|---|---|---|
| 4443182C2 | 1/1998 | (DE) . |

* cited by examiner

Primary Examiner—John G. Weiss

(57) ABSTRACT

A device for conducting away urine and excrera to be used by a person relieving him or herself, consisting of sheet material having a top portion (11) with an inlet opening (12) and a bottom portion (11a) with a discharge opening (14) and a surface area (21) having coated theron an adhesive substance (19) to facilitate the opening of inlet (12). Further, the device is useful for the disposal of excrements by a being particularly a human having an artificial intestinal or urethral orifice.

24 Claims, 3 Drawing Sheets

URINE AND EXCRETA DISPOSAL DEVICE AND METHOD OF USE

BACKGROUND OF THE INVENTION

1. Field of the Invention

The present invention relates to a device can be to be used for conducting away urine and excreta by a person relieving him or herself, said device assembled from a sheets of web material to form funnel shaped hose structure having cop and bottom portions with inlet and discharge openings thereat, respectively.

The present invention was devised to serve persons who for whichever reason wish to urinate while standing up or to empty a device such as a stomal collection bag (stoma bag) as discrietly as possible. Due to the free fall height and the dispersion angle, which is difficult to control, the substance to be evacuated often sprays and splashes about in the form of droplets that end up outside the toilet bowl or on the user's clothes.

2. Background Art

DE 43 43 789 C2 discloses a urine discharge device comprising a flexible hose member having openings at both ends and made of a material which dissolves in water at least partly and with some delay. This urine discharge device in hose form has a funnel shaped inlet, manual holding means at the top as well as a discharge opening in its bottom portion.

DE 44 43 182 C2 discloses a device for accepting and discharging urine from a person particularly a human male relieving himself. This prior device comprises a flexible hose element made of a sheet of a web material such as paper folded to form two superimposed layers and having a manual holding portion, an inlet portion and a discharge portion. A multitude of said layers are integrally connected together in a longitudinal channel at their common front edge in a quasi endless succession, U.S. Pat. 4,608,046 discloses a device for evacuating urine from women which comprises a tube to be introduced in the labia. This tube is flexible in order to con form to the individual user's physical features.

All these above described prior devices present a major problem when the inlet is to be opened. With the device collapsed and flat, the device is space saving and inexpensive to transport and simple to store; in contrast, spreading it to open the inlet is complicated as the user usually has only one free hand to accomplish the task.

SUMMARY OF THE INVENTION

It is an object of the present invention to provide a device for reducing the fall height of and conducting body excreta of which the inlet opening is easy to open.

This object is achieved by a coat of an adhesive substance applied to the surface of the web material in the general region of the inlet opening The aforesaid adhesive substance is provided in the top area adjacent the inlet opening. It extends horizontally and circumferentially in an adhesion area on the surface, whereby the user can rub his or her thumb and index finger against each other to exert on the folded together or collapsed device a force sufficient to form an opening in the inlet area.

Beings and particularly humans whose ureter or lower intestine is made by surgery to open at an unnatural location on the body surface often experience major problems when they attempt to dispose their excreta in a controlled and discrete manner. These individuals have had sections of their lower intestine removed by surgery to remove an intestinal cancer. In the process, the intestinal or urethral orifice is artificially relocated on the abdomen and provided with a discharge valve to which a catheter may be connected when needed. This arrangement greatly impedes a dosed discharge of the excreta.

The problem can be solved by means of a device consisting of a sheet material which dissolves in water at least partly and with some delay, the device forming a flexible hose with a top portion having an inlet therein and a bottom portion having a discharge opening therein and being used for conducting excrera away from a being's artificial intestinal or urethral orifice.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

Further advantageous measures are described in the dependent claims. The invention is shown and illustrated in the attached drawing and will be described in greater detail hereinbelow.

DETAILED DESCRIPTION OF THE PREFERRED EMBODIMENTS

Figure 1:
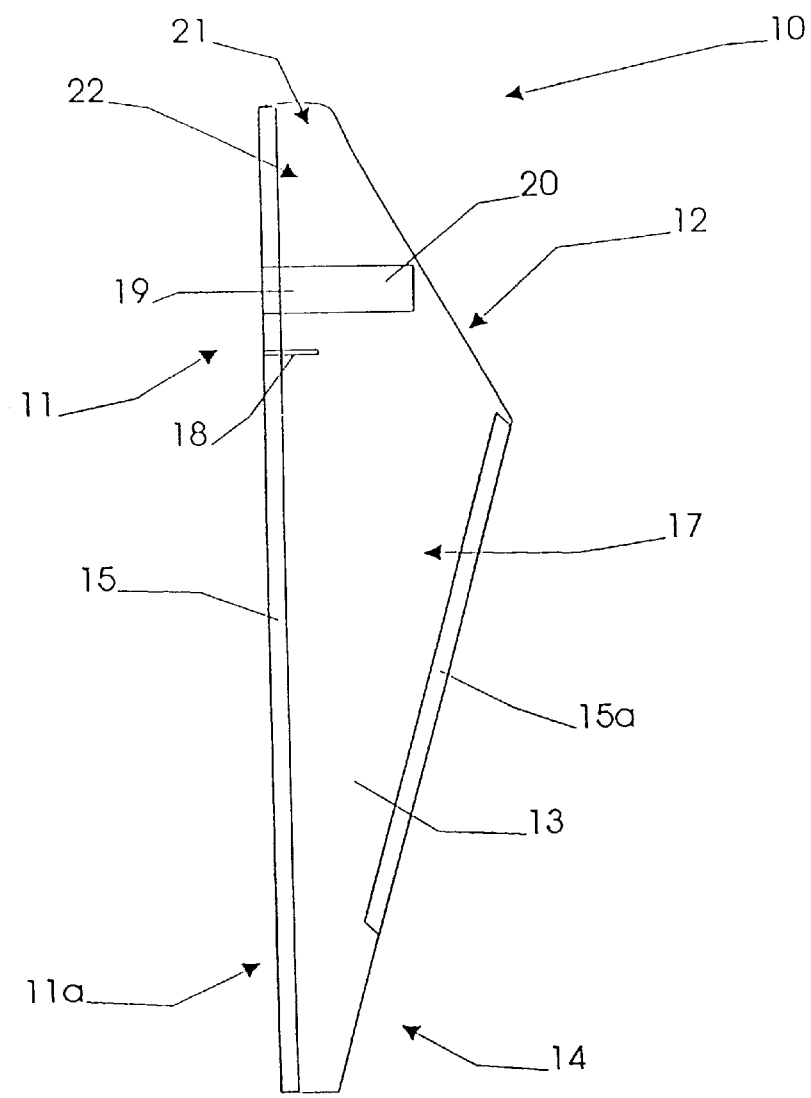
FIG. 1 is a side view showing the inventive urine conducting device as having a top portion with an inlet opening and a bottom portion with a discharge opening, there also being provided an incision and an adhesion area having an adhesive substance applied thereon.

As shown in FIG. 1. urine conducting device 10 comprises downwardly tapered sheets 16, 17, For forming conducting hose structure 13, sheets 16, 17 are placed on top of each other to be coextensive and are joined along their edges by sections of seam 15, 15a.

Figure 3:
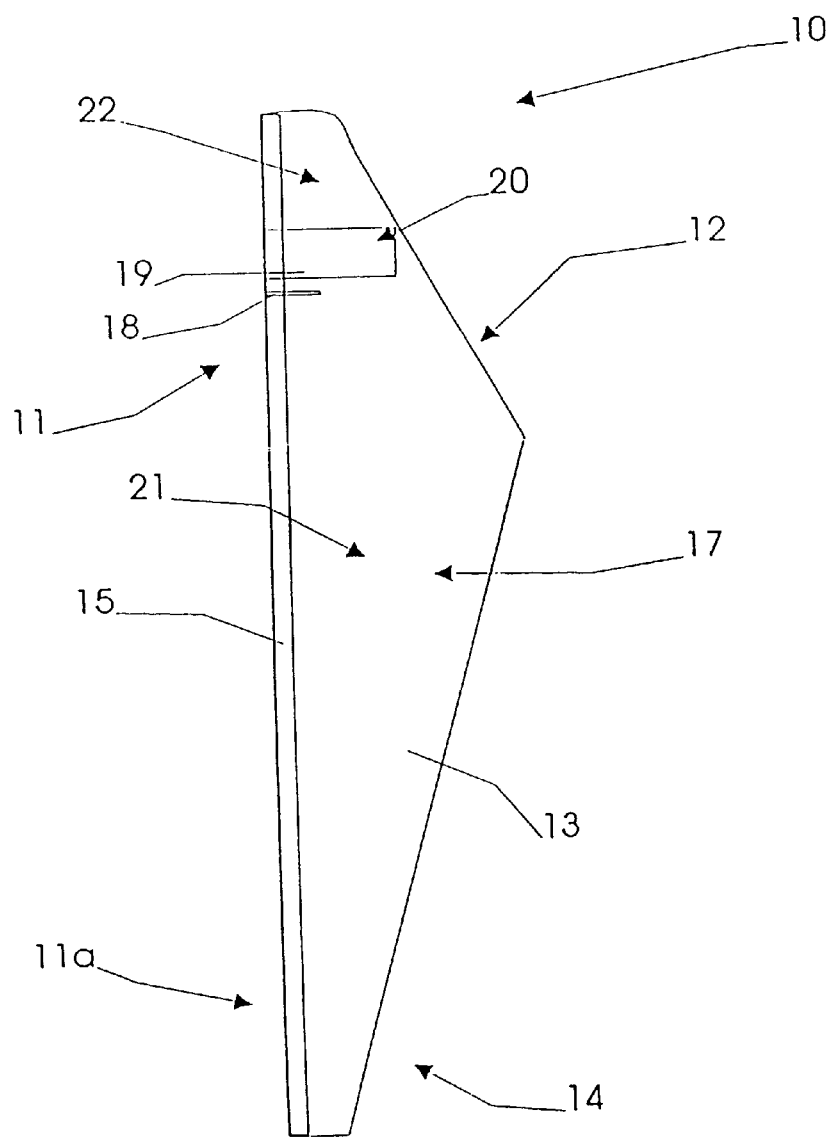
FIG. 3 is a side view showing the urine conducting device of FIG. 1 with an adhesion area above the incision, but without a front scam.

FIG. 3 shows an embodiment of inventive urine conducting device 10 in which sheets 16, 17 are joined along a single seam 15 only at the front This embodiment is very simple and inexpensive to fabricate as joining is needed along one seam only.

In its top portion 11, urin conducting device 10 has an inlet opening 12 therein. Inlet opening 12 is arranged to be angled upwards towards the vertically extending connecting seam 15, whereby urine conducting device 10 will be oriented away from the user's body after he has introduced his penis in the device.

In its bottom portion 11a, urine conducting device 10 has a discharge opening 14 from which urine can be directed into a collecting fixture such as a toiler bowl (not shown).

Figure 2:
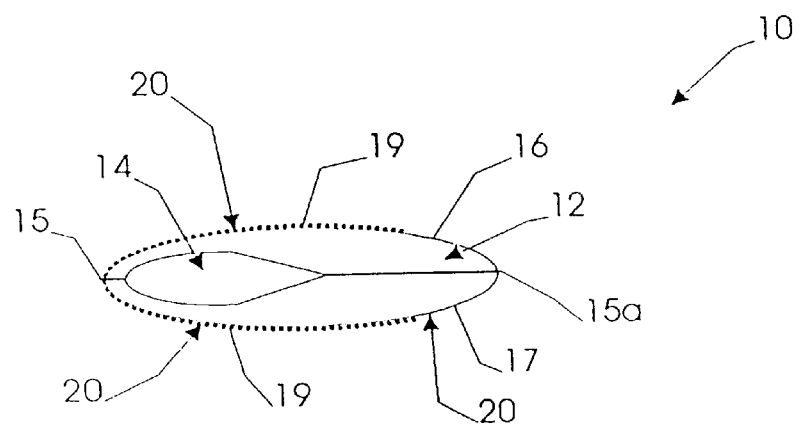
FIG. 2 is a top view showing the urine conducting device of FIG. 1.

In top portion 11 and in the general area of inlet opening 12, there is provided a horizontal adhesion area 20 coated with an adhesive material 19. As shown in FIG. 2, adhesion area 20 extends circumferential of surface 21 of device 10. Adhesion area 20 preferably has the form of a stripe of material. The bonding power of adhesive substance 19 is rather low and merely increases the surface friction in adhesion area 20 relative to the remaining surface 21.

The adhesive material or agent 19 preferably is provided within adhesion area 20. For use by the end consumer, a great number of urine conducting devices 10 are wound up to form a coil, as is toilet paper, for example, or packed in a box.

To keep the individual urine conducting devices from sticking to each other in the package, the adhesive substance should have have dried less than one minute after having been applied and the devices having been packaged. One exemplary adhesive agent 19 having the afore said properties is gumming or a coat of molasses. Coatings of this nature impart resistance to moisture for a certain period of time before finally dissolving without leaving residues. This enables a simple disposal of the inventive devices to be obtained by simply flushing them down a toilet.

Another possibility of facilitating the opening of the device at the inlet is to mechanically or chemically roughen surface 21 of sheets 16, 17 in the bonding area. This may be accomplished by start grinding these surface portions or by applying a grip imparting liquid to them.

A substantially horizontally extending slit or incision 18 is provided to keep moisture and particularly urine from rising in sheets 16, 17 as these get to be moist in use. Incision 18 delimits a manual holding portion 22 extending downwardly from the top edge of device 10.

The substantially hoirzontally extending incision 18 interrupts the capillaries existing within the body of sheets 16, 17, whereby rising moisture is kept away from manual holding portion 22 and the user's angers.

Adhesion area 20 is provided to lie above incision 18 so that bonding agent 19 can be used not only for opening inlet 12 but also for safely holding device 10 by one's fingers.

Figures 4, 5:
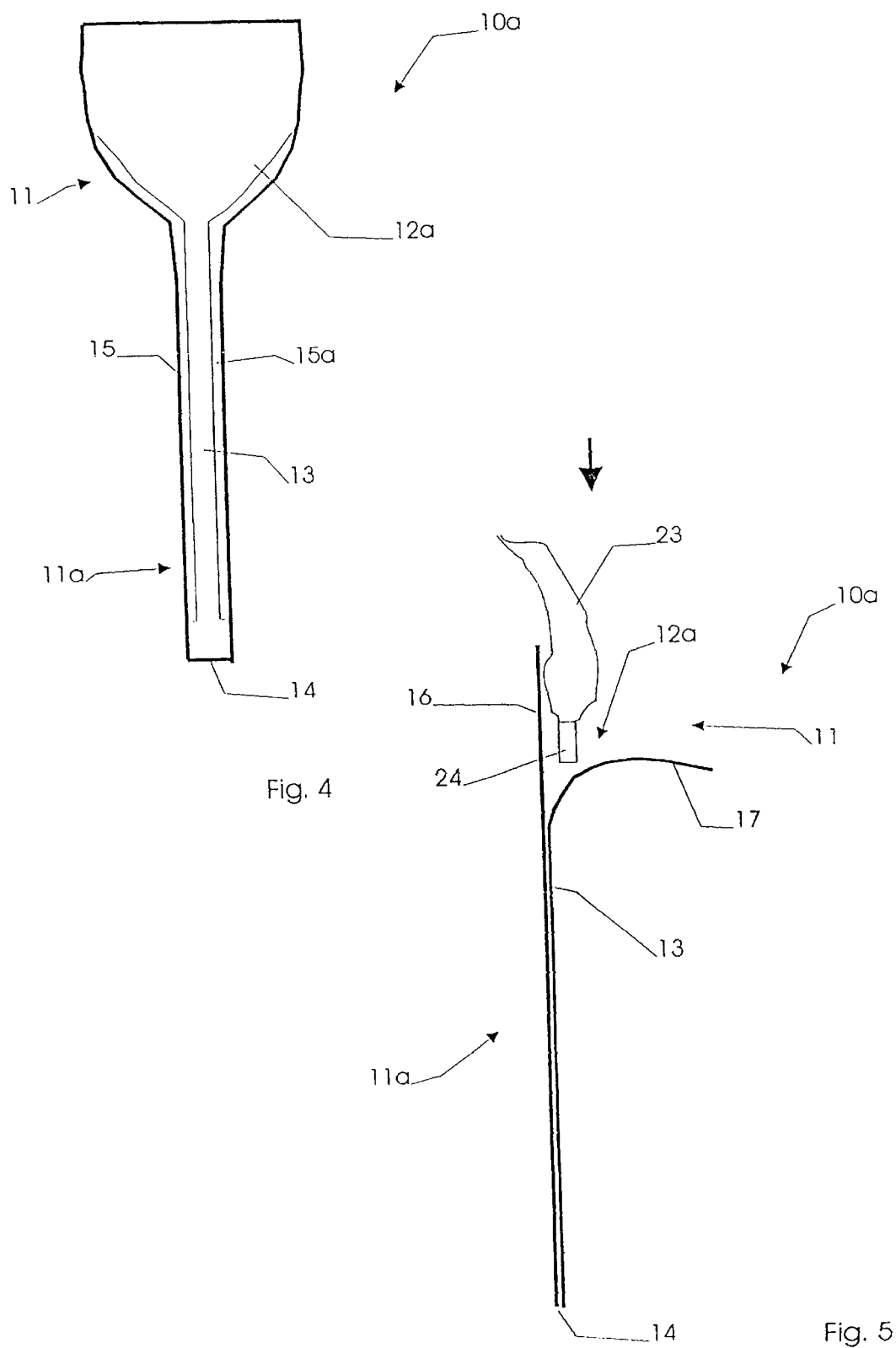
FIG. 4 shows an elevation of an excreta conducting device with folded-up inlet structure.
FIG. 5 shows a side view of an excreta conducting device with the inlet opening folded up and the collection bag to be emptied introduced therein.

FIGS. 4 & 5 show a device useful for the disposal of feces collected by means of a stomal collection bag 23. To this end, top portion 11 of disposal device 10a is provided with an inlet opening 12a expanded to form a funnel For disposal, and as shown in FIG. 5, front sheet 17 is withdrawn in a direction away from the user's body (not shown) and rear sheet 16 pulled up under collection bag 23. Thereafter, opening 24 of collection bag 23 is introduced between the two sheets and front sheer 17 then turned up again. This way, opening 24 of stoma bag 23 comes to lie directly above the inlet of hose device 13, whereby the contents of the stoma bag can be disposed of cleanly and without splashing To facilitate the downward conduction and egress of solid or pasty components from stoma bag 23, hose device 13 is expanded in the bottom portion 11a and at the discharge opening 14 thereof. To prevent sheets 16, 17 from prematurely absorbing major amounts of moisture, the internal surfaces thereof are coated preferably with molasses, a natural residue from the processing of sugar beers. This coating retards the absorption of moisture by the sheet material and will dissolve completely and virtually without residues, thus meeting environmental requirements.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

| List of Reference Numerals | |
| --- | --- |
| 10 | urine conducting device |
| 10a | excreta conducting device |
| 11 | top portion |
| 11a | bottom portion |
| 12 | inlet opening |
| 12a | folding inlet opening |
| 13 | discharge hose |
| 14 | discharge opening |
| 15, 15a | connecting seam |
| 16, 17 | sheet |
| 18 | incision |
| 19 | adhesive substance |
| 20 | adhesive-coated area |
| 21 | surface |
| 22 | manual holding area |
| 23 | stoma bag |
| 24 | opening of a stomal bag |

What is claimed is:

1. A device for conducting urine or excreta to be used by a user relieving him or herself, the device comprising:
   at least one sheet of web material forming a hollow structure having an interior and an exterior surface;
   an inlet opening at a top portion of the device, the inlet opening being adapted to face a user's body during conduction of urine or excreta away from the user's body;
   a discharge opening at a bottom portion of the device; and
   an adhesive substance disposed on the exterior surface of the hollow structure, wherein
   the adhesive substance is disposed on said exterior surface of the hollow structure so that at least a part of an exterior surface of the adhesive substance faces generally away from the inlet opening and generally away from the user's body during use of the device, and
   the adhesive substance is disposed on the exterior surface of the hollow structure so that that a user can grasp the adhesive substance during use of the device.

2. The device for conducting urine or excreta according to claim 1, wherein the top portion of the device includes a manual holding area proximate to the inlet opening, the adhesive substance being disposed on the manual holding area.

3. The device for conducting urine or excreta according to claim 2, wherein the adhesive substance includes a coat of adhesive.

4. The device for conducting urine or excreta according to claim 2, wherein the adhesive substance is a material selected from the group consisting of gumming and molasses.

5. The device for conducting urine or excreta according to claim 2, wherein the at least one sheet of web material is joined at a first seam extending at least substantially from the top portion to the bottom portion of the device.

6. The device for conducting urine or excreta according to claim 5, wherein the at least one sheet of web material includes a sheet of web material which is folded such that edges of the sheet are joined at the first seam, the first seam extending along the hollow structure on a side of the hollow structure which is opposed to a side of the hollow structure which includes the inlet opening, at least a portion of the adhesive substance being disposed across said first seam.

7. The device for conducting urine or excreta according to claim 5, wherein the at least one sheet of web material includes two sheets of web material which are joined at the first seam, and at a second seam.

8. The device for conducting urine or excreta according to claim 7, wherein the inlet opening is angled upwardly from the second seam towards the first seam, the adhesive substance being disposed on said exterior surface of the hollow structure at a location that is closer to the first seam than to the second seam.

9. The device for conducting urine or excreta according to claim 7, wherein the two sheets of web material have edges which are substantially coextensive, the sheets being joined at two edges by the first and second seams.

10. The device for conducting urine or excreta according to claim 5, wherein the adhesive substance is in the form of a stripe coating of adhesive material, the stripe extending transversely to the first seam.

11. The device for conducting urine or excreta according to claim 2, further including an incision extending across the at least one sheet, the incision being located between the discharge opening and the manual holding area.

12. The device for conducting urine or excreta according to claim 2, further including a coating disposed on the interior surface of the hollow structure, the coating retarding absorption of moisture by the at least one sheet of web material.

13. The device for conducting urine or excreta according to claim 1, wherein the hollow structure includes a first edge which faces generally away from the user during use of the device, and a second edge on a side of the hollow structure opposed to the first edge, the second edge being on the same side of the hollow structure as the inlet opening, and the adhesive substance is disposed on the exterior of the hollow structure at a location which is closer to the first edge than to the second edge.

14. The device for conducting urine or excreta according to claim 13, wherein the first edge includes a seam joining edges of the at least one sheet of web material.

15. A device for conducting urine or excreta to be used by a user relieving him or herself, the device comprising:

at least one sheet of web material forming a hollow structure having an interior and an exterior surface;

an inlet opening at a top portion of the device;

a discharge opening at a bottom portion of the device; and a manual holding area proximate to the inlet opening; wherein the exterior surface of the hollow structure includes a roughened area which facilitates an opening of the inlet opening.

16. The device for conducting urine or excreta according to claim 15, wherein the roughened area is formed by grinding or by chemical treatment.

17. The device for conducting urine or excreta according to claim 15, wherein the device includes a first edge which faces generally away from the user during use of the device, and a second edge on a side of the hollow structure opposed to the first edge, the second edge being on the same side of the hollow structure as the inlet opening, and the roughened area is disposed on the exterior of the hollow structure at a location which is closer to the first edge than to the second edge.

18. The device for conducting urine or excreta according to claim 17, wherein the first edge includes a seam joining edges of the at least one sheet of web material.

19. A device for conducting excreta away from a being's artificial intestinal or urethral orifice comprising:

a sheet material forming a flexible hose structure;

an inlet opening at a top portion of the structure; and a discharge opening at a bottom portion of the structure; wherein the bottom portion has an interior cross sectional area adjacent to the discharge opening which is less than an interior cross sectional area of the discharge opening.

20. The device for conducting excreta according to claim 19, wherein the sheet material includes two sheets joined along edge surfaces of each sheet by connecting seams.

21. The device for conducting excreta according to claim 20, wherein the connecting seams extend substantially from the inlet opening to the discharge opening, the seams being located on opposed edges of the sheets, and defining the interior cross sectional area of the bottom portion of the structure, and the discharge opening is located at a point at which the connecting seams terminate on the bottom portion of the structure.

22. The device for conducting excreta according to claim 20, wherein the top portion of the structure includes a folding inlet opening forming a portion of the inlet opening, the inlet opening folding at a point which the connecting seams terminate on the top portion of the structure.

23. The device for conducting excreta according to claim 20, further including a coating of material on the interior surface of the hose structure, the coating of material acting to retard the absorption of moisture by the sheet material.

24. The device for conducting excreta according to claim 19, wherein the sheet material dissolves in water after a delay period.

* * * * *